(12) United States Patent
Lemer

(10) Patent No.: US 8,439,815 B2
(45) Date of Patent: May 14, 2013

(54) MEDICAL UNIT FOR WITHDRAWAL, CALIBRATION, DILUTION AND/OR INJECTION OF AN INJECTABLE RADIOACTIVE PRODUCT

(75) Inventor: Pierre-Marie Lemer, Nantes (FR)

(73) Assignee: Lemer Protection Anti-X Par Abreviation Societe Lemer Pax, Carquefou (FR)

( * ) Notice: Subject to any disclaimer, the term of this patent is extended or adjusted under 35 U.S.C. 154(b) by 1021 days.

(21) Appl. No.: 12/443,272

(22) PCT Filed: Sep. 28, 2007

(86) PCT No.: PCT/FR2007/052048
§ 371 (c)(1),
(2), (4) Date: Mar. 27, 2009

(87) PCT Pub. No.: WO2008/037939
PCT Pub. Date: Apr. 3, 2008

(65) Prior Publication Data
US 2010/0030009 A1    Feb. 4, 2010

(30) Foreign Application Priority Data
Sep. 29, 2006 (FR) ...................................... 06 08586

(51) Int. Cl.
*A61M 3/00* (2006.01)
(52) U.S. Cl.
USPC ........................................ 600/4; 250/432 R
(58) Field of Classification Search .................. 600/1–8; 250/328, 428, 430–432 R, 434–436
See application file for complete search history.

(56) References Cited

U.S. PATENT DOCUMENTS

| | | | |
|---|---|---|---|
| 5,039,863 A | | 8/1991 | Matsuno et al. |
| 5,472,403 A | * | 12/1995 | Cornacchia et al. ............... 600/4 |
| 5,514,071 A | * | 5/1996 | Sielaff et al. ...................... 600/3 |
| 5,961,439 A | * | 10/1999 | Chernomorsky et al. ......... 600/4 |
| 6,450,936 B1 | * | 9/2002 | Smith et al. ........................ 600/4 |
| 6,468,219 B1 | | 10/2002 | Njemanze |
| 6,767,319 B2 | | 7/2004 | Reilly et al. |
| 2005/0085682 A1 | | 4/2005 | Sasaki et al. |
| 2005/0278066 A1 | | 12/2005 | Graves et al. |

FOREIGN PATENT DOCUMENTS

| | | |
|---|---|---|
| DE | 20 2005 008 379 | 8/2005 |
| FR | 2 739 565 | 4/1994 |
| FR | 2 867 294 | 9/2005 |

OTHER PUBLICATIONS

International Search Report dated Mar. 25, 2008, from corresponding PCT application.

* cited by examiner

*Primary Examiner* — Charles A Marmor, II
*Assistant Examiner* — Carrie R Dorna
(74) *Attorney, Agent, or Firm* — Young & Thompson

(57) ABSTRACT

A medical unit includes a shielded enclosure (2) in which are accommodated:—elements (13) for supporting a container (12) including a source or a generator of injectable radioactive product (11),—elements (10) for supporting a syringe (6),—a device (3) of the activimeter type, and—a system of pipes (9, 20, 23, 24) associated with at least one valve (15). The syringe support (10), the valve (15) and the radioactive source support (13) are arranged vertically relative to one another, respectively from top to bottom, the syringe support (10) being arranged to support the syringe (6) with the plunger (8) thereof oriented upward. The valve (15) and the syringe plunger (8) can be operated so as to ensure the withdrawal, dilution and injection operations.

19 Claims, 2 Drawing Sheets

MEDICAL UNIT FOR WITHDRAWAL, CALIBRATION, DILUTION AND/OR INJECTION OF AN INJECTABLE RADIOACTIVE PRODUCT

BACKGROUND OF THE INVENTION

1. Field of the Invention

The present invention relates to the general field of nuclear medicine. More particularly, it relates to a medical unit utilized for withdrawal, calibration, dilution and/or injection of a radioactive substance intended for being injected to a patient.

2. Description of the Related Art

Some radioactive substances are particularly useful in the medical field, for example in imaging procedures, as contrast agents or as therapeutic agents.

In order to limit the doses of radiations received by the patient and by the personnel in charge of the manipulations, use is made of medical-use short half-life radioelements, namely radioactive products whose level of emitted radiation decreases rapidly with time.

But, with such short half-life radioactive products, it is problematic to administer a suitable dose to the patient. The corresponding dosage must be very precise; it must take into account the time necessary for preparing the dose to be injected as well as the possible time between the moment of preparation of the product dose and the moment of injection itself of this dose to the patient.

Further, despite the type of products implemented (short half-life), another constraint to be taken into account relates the radioprotection of the medical personnel in charge with the preparation of the radioactive dose and the injection of it to the patient. This radioprotection has also to be effective for the patient.

In a classical manner, the doses to be injected are withdrawn in a syringe provided with a suitable shielding and placed itself in a shielded enclosure equipped with suitable measuring and controlling means that enable the aimed dose of radioactive product to be withdrawn. Next, an operator picks up the shielded syringe and goes to the patient to make the injection.

However, this way of proceeding does not offer an optimal security, as far as both operator radioprotection and precision of the dose injected to the patient are concerned.

Document U.S. Pat. No. 6,767,319 describes an equipment for calibration and injection of a radioactive product, aiming to limit personnel exposure to the radioactive substance and also to optimize the patient security.

The corresponding installation comprises three separate radioprotective enclosures, each including:
- means for supporting a source of injectable radioactive product,
- means for supporting a syringe, that are equipped with means for automatic operation of the plunger of the latter and that are associated with a device of the activimeter type for measuring in real time the radioisotopic activity from the product contained in the syringe, and
- a system of valves.

This system of valves is hydraulically connected, through tubes, to the enclosure containing the radioactive mother source, to the enclosure containing the syringe, to a source of physiological saline solution and to an injection catheter intended for being connected to the patient.

This equipment further comprises means intended for driving the system of valves and the means for operating the syringe plunger, in such a way to ensure, in a first time, withdrawal of a dose of radioactive product and/or of physiological saline solution into the syringe, and in a second time, ejection of the withdrawn radioactive product and/or physiological saline solution through the injection catheter. The dose of radioactive product is measured by the activimeter device during withdrawal into the syringe.

In this equipment, the tubes that connect the enclosure containing the system of valves and those containing the syringe or the radioactive source are not protected and are sources of radioactive emissions into the environment. Moreover, because of the structure thereof, the corresponding equipment is cumbersome. Further, complexity of the network of tubes leads to the presence of significant dead volumes.

BRIEF SUMMARY OF THE INVENTION

The present invention provides a novel very compact-size medical unit for calibration and injection of radioactive products, that allows withdrawal, measuring and injection of products with a great precision, in complete safety, and with reduced dead volumes.

This medical unit is of the type comprising:
- means for supporting a container made of a radioprotective material, in which is accommodated a source or a generator of injectable radioactive product,
- means for supporting a syringe equipped with a plunger,
- a device of the activimeter type for measuring in real time the radioisotopic activity from the contents of said syringe, and
- a system of pipes associated with at least one valve for hydraulic connection of said radioactive source, of said syringe, of a source of physiological saline solution and of an injection catheter intended for being connected to the patient, wherein said valve and said syringe plunger can be operated to ensure, on the one hand, aspiration of said radioactive product or said physiological saline solution into said syringe, and on the other hand, ejection, through said injection catheter, of said radioactive product, said physiological saline solution or a mixture of both, beforehand aspirated into said syringe, the dose of radioactive product withdrawn and injected by said syringe being measured by said activimeter.

According to the invention, the medical unit further comprises a shielded enclosure made of at least one radioprotective material, in which are accommodated the radioactive source support, at least one part of the means for supporting the syringe, the activimeter, the valve and at least one part of the system of pipes.

Moreover, the syringe support, the valve and the radioactive source support are arranged vertically relative to one another, respectively from top to bottom, the syringe support being arranged to carry the syringe vertically with the plunger thereof oriented upward.

This particular arrangement enables the withdrawal/injection syringe and the radioactive product source to be close to the valve, which offers a very compact-size unit, with minimized dead volumes.

According to an embodiment feature, the valve consists in a three-way valve comprising:
- an upper way, intended for being connected to the withdrawal and injection syringe,
- a lower way, intended for being connected to the source of injectable radioactive product, and
- a side way, intended for being connected to a first pipe connected to the source of physiological saline solution and to a second pipe connected to the injection catheter, said pipes being each equipped with a suitably oriented check valve.

In this case, the activimeter has advantageously a generally tubular shape circumscribing a vertical-axis central well intended for containing the syringe, said activimeter being provided with two openings, an upper one and a lower one, the latter being directed opposite the three-way valve and the radioactive source support.

To reduce the dead volumes in the pipes of this equipment, the upper way of the valve, intended for being connected to the syringe, advantageously comprises a tight membrane seal intended for being pierced by the needle fitting said syringe mounted on the support thereof; likewise, the lower way of the valve, intended for being connected to the source of radioactive product is advantageously extended with a needle intended for piercing a membrane seal closing the vial that contains said radioactive source.

According to another embodiment feature of the invention, the radioactive source and syringe supports are each carried by means ensuring displacement(s) thereof along a vertical or substantially vertical axis, between two positions:

a first position, in which an operator can install the radioactive source and the syringe onto the respective supports thereof, or inversely to remove them, and a second position, in which the radioactive source and the syringe are connected to the valve.

According to this feature, the means for displacing the syringe support advantageously enable the later to travel vertically through an orifice arranged in the shielded closure, between:

an upper installing/removing position, in which said support is located at least partially outside said enclosure, and a lower connecting position, in which the syringe is positioned inside the central housing of the activimeter and is connected to the valve.

Moreover, the radioactive source support advantageously travels inside the shielded enclosure between the installing/removing and connecting positions thereof; this enclosure is further provided with a front trap door for enabling an operator to reach the radioactive source support at least when the latter is in the installing/removing position thereof.

According to still another feature, the medical unit comprises computer and/or electronic control means able to drive the valve and the means for operating the syringe plunger, in order for the withdrawal and ejection operations of the syringe to be performed. Likewise, the computer/electronic control means possibly also drive the means for displacing the syringe support and the radioactive source support.

In this case, the means for operating the syringe plunger are advantageously of the disengageable gear motor type, controlled by the computer/electronic means, to ensure, on the one hand, automatic withdrawal of a definite dose of radioactive product into the syringe, and on the other hand, injection of this dose to the patient, either automatically or manually. Indeed, the operator, if he or she wants, can disengage the gear motor means and manually control injection of the radioactive dose to the patient.

According to another interesting embodiment, the enclosure consists in three sub-enclosures aligned vertically relative to one another, namely:

an upper sub-enclosure containing the syringe and the activimeter, an intermediate sub-enclosure containing the valve, and a lower sub-enclosure containing the source of radioactive product.

These sub-enclosures are connected together two by two via through-openings through which pass some of the hydraulic connecting pipes.

To further optimize processing of the medical data, the computer/electronic control means are provided with connectics for sending and/or receiving data, in particular for exchanges with a computer server.

The medical unit according to the invention can be rendered mobile. To that end, it is mounted on advantageously motor-driven wheels; it possibly integrates a geolocation system, for example of the GPS type.

BRIEF DESCRIPTION OF THE DRAWINGS

The invention will be further illustrated, without being in any way limited, by the following description of a particular embodiment, given only by way of example and shown in the attached drawings, in which.

DETAILED DESCRIPTION OF THE PREFERRED EMBODIMENTS

Figure 1:
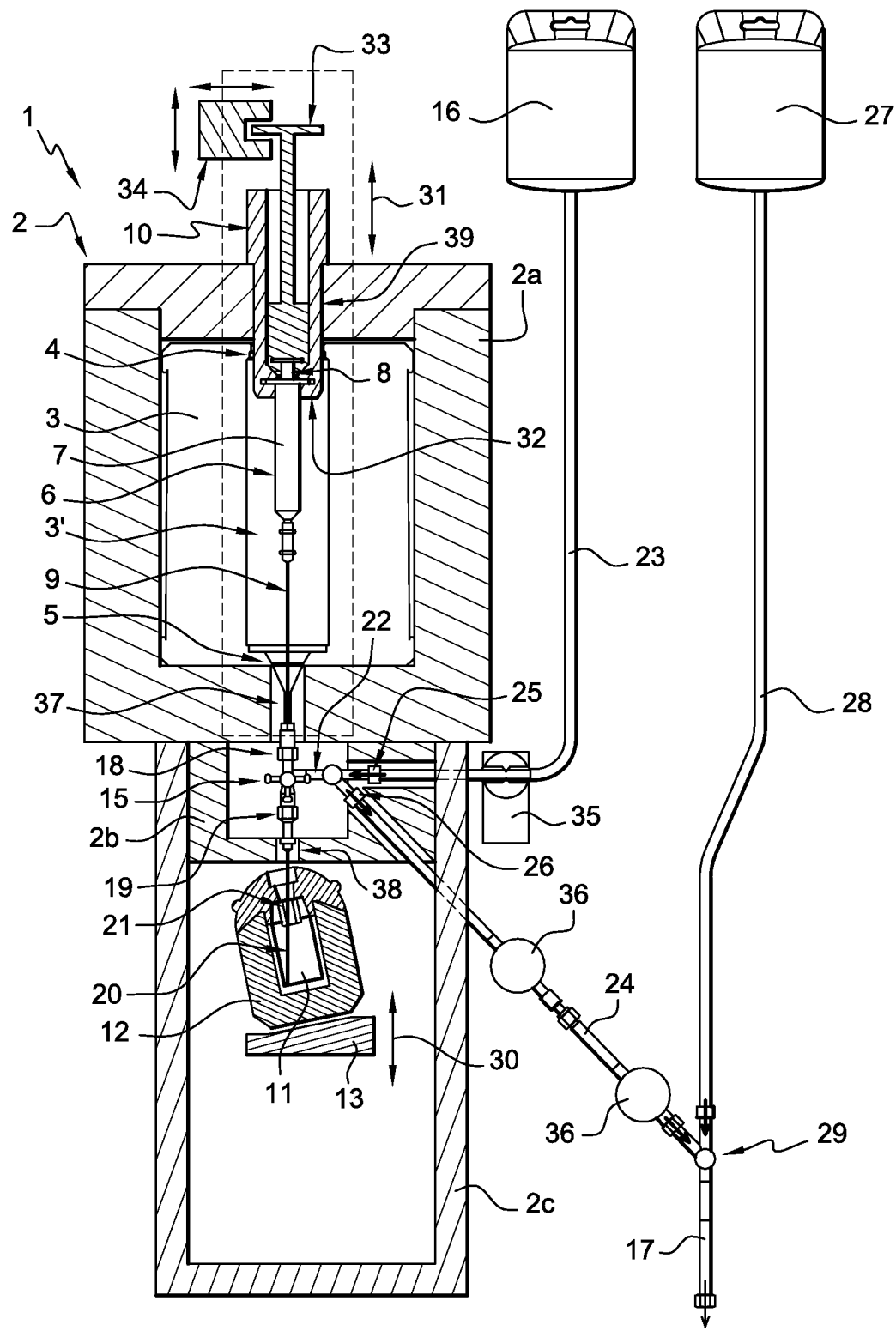
FIG. 1 is a sectioned schematic view of a medical unit according to the invention.

As shown in FIG. 1, the medical unit 1 according to the invention comprises a shielded enclosure 2 made of a radio-protective material, in which is located a device 3 for measuring in real time the radioisotopic activity (activimeter of the ACAD type (registered trademark)), that has a generally vertical-axis cylindrical shape and that is provided with an upper opening 4 and a lower opening 5.

A conventional syringe 6, comprising a body 7, a plunger 8 and a needle 9, is installed in the measuring well 3' of the activimeter 3 (and is connected to a suitable processing unit); this syringe 6 is mounted vertically on an upper support 10, with the plunger 8 thereof oriented upward and the needle 9 thereof thus oriented downward.

A source or generator 11 of radioactive product is placed under the activimeter 3, opposite the lower opening 5 of the latter. This radioactive product source 11 is contained in a vial conditioned inside a shielded container 12 made of a radio-protective material. The shielded container 12 is accommodated in the shielded enclosure 2 and placed on a support 13.

A motor-driven three-way valve 15, accommodated in the shielded enclosure 2 between the syringe 6 and the vial of radioactive source 11, ensures a suitable hydraulic connection between said syringe 6, said vial of radioactive source 11, a physiological saline solution bag 16 (external to the shielded enclosure 2) and an catheter 17 for injection to the patient (also external to the shielded enclosure 2). The valve 15 is located opposite the lower opening 5 of the activimeter 3 and opposite the radioactive source 11.

The upper way 18 of this three-way valve 15 comprises a tight membrane seal intended for being pierced by the needle 9 of the syringe 6. The lower way 19 of the valve 15 is extended with a needle 20 intended for piercing the tight membrane seal 21 closing the vial of radioactive source 11. The side way 22 of the valve 15 is connected, through a Y-connector, to a tube 23 leading to the physiological saline solution bag 16 and to a tube 26 leading to the injection catheter 17. The tube 23 is equipped with a check valve 25 preventing liquid returning toward the physiological saline solution bag 16. The tube 24 is also equipped with a check valve 26 forcing the liquid to go toward the patient.

It can be seen in FIG. 1 that the catheter 17 is also in communication with a second physiological saline solution bag 27, through a tube 28 and a Y-connector 29.

The three-way valve 15 has two main positions:—a first position, in which the upper 18 and lower 19 ways thereof are in communication (which enables the syringe 6 to be placed in communication with the radioactive product source 11 to ensure withdrawal of a dose of radioactive product into the syringe body 7), and—a second position, in which the upper 18 and side 22 ways are in communication (either to aspirate physiological saline solution from the bag 16 into the syringe body 7, during an aspiration operation by the syringe 6, or to eject the liquid contained in the syringe body 7 into the injection catheter 17, through a draining operation of the syringe body 7).

A third possible position of the valve 15 consists in placing the radio-element source 11 and the tubes 23 and 24 in communication, so as to break the vacuum inside the vial of radioactive source 11 while allowing aspiration of the physiological saline solution from the bag 16.

The three-way valve 15 is fixedly secured inside the enclosure 2, on the vertical or substantially vertical axis running through the syringe 6 and the radioactive product source 11.

The support 13 of the radioactive product source 11 is mobile in the vertical direction, according to the orienting arrow 30, under the action of suitable mechanical means (not shown) actuated by hand (or by foot) or by motor means (not shown either), so as to enable introduction of the needle 20 into the vial of radioactive source 11 or extraction of this needle 20 from said vial.

The operator operates the mobile support 13 in this later "extracted" position when he or she wants to change the radioactive product source.

On the other hand, the support 10 of the syringe 6 is also mobile in the vertical direction, according to the orienting arrow 31, under the action of suitable mechanical means (not shown) actuated by hand or by motor means (not shown either), so as to enable introduction of the needle 9 of the syringe 6 into the three-way valve 15 or extraction of the syringe 6 above the activimeter 3 and outside the shielded container 2, for installation and removal of the syringe 6.

The support 10 of the syringe 6 is further arranged to allow an operation of the syringe plunger 8 from the outside of the shielded container 2, when said syringe 6 is centred in the measuring well 3' of the activimeter 3.

To that end, the support 10 comprises a cylindrical part 32 engaging with the rear part of the syringe body 7, and a central part 33, in the form of a plunger sliding into the cylindrical part 32, engaging with the rear part of the syringe plunger 8.

When the syringe body 7 is in position inside the measuring well 3' of the activimeter 3, the upper end of the sliding plunger 33 can be reached from the outside of the shielded container 2. This plunger 33 upper end is associated with a disengageable motor system 34 which, once engaged, allows automatic operation of the syringe plunger 8 and which, when disengaged, allows manual operation of this plunger 8.

This particularity enables the operator to choose between automatic and manual management of the radioactive product withdrawal by the syringe 6 and/or of the product ejection into the catheter 17.

It can be noticed in FIG. 1 that a solenoid pinch valve 35 is positioned in the tube 23 of the physiological saline solution bag 16. The function of this solenoid valve 35 is to prevent untimely circulation of physiological saline solution through the tube 23 before connection of the injection catheter 17 to the patient.

It can also be noticed that two bubble preventing/antibacterial means 36, for example in the form of filters, are present on the feeding tube 24 of the catheter 17 to ensure the sterility of the injection process.

Still in FIG. 1, it can be seen that the shielded enclosure 2 is in the form of three shielded sub-assemblies:
- a first assembly 2a integrates the activimeter 3 and a part of the syringe support 10,
- a second assembly 2b encloses the motor-driven three-way valve 15, and
- a third assembly 2c encloses the mobile support 13 with the shielded container 12 thereof.

The three sub-enclosures 2a, 2b and 2c are stacked; the syringe 6 and the valve 15 are connected through an opening 37 arranged between said sub-assemblies 2a and 2b. The valve 15 and the radioactive product source 11 are connected through an opening 38 arranged between the sub-assemblies 2b and 2c.

The support 10 of the syringe 6 is made of a radioprotective material. The size thereof maximally fits in an opening 39 arranged in the upper part of the sub-assembly 2a, to provide a shielding continuity in the lowered position (that is when the syringe 6 is centred in the measuring well 3' of the activimeter 3).

The shielded enclosure 2 further comprises openings adapted for the tubes 23 and 24, linked to the physiological saline solution bag 16 and to the catheter 17 respectively, to go through.

The main steps implemented in the medical unit 1 for preparation of a definite dose of radioactive product and then injection thereof to the patient will now be described in detail.

Firstly, the dose of radioactive product to be injected to the patient is prepared inside the syringe 6.

To that end, the syringe 6 (with the plunger 8 thereof in low position) and the radioactive product source 11 are connected to the three-way valve 15; next, this valve 15 is driven so as to hydraulically connect the upper 18 and lower 19 ways thereof together, which enables the syringe needle 9 to communicate with the radioactive product source 11.

The syringe plunger 8 is next operated, upward, to aspirate into the syringe body 7 the desired dose of radioactive product, which is measured in real time by the activimeter 3. This dose is notably function of the patient's weight.

The dose prepared inside the syringe can next be administered to the patient.

To that end, the valve 15 is again driven so as to place the upper 18 and side 22 ways thereof in communication with the syringe needle 9 and with the tubes 23 and 24 (connected to the physiological saline solution bag 16 and to the injection catheter 17), respectively.

Before the injection phase itself, if necessary, the syringe plunger 8 can be driven (upward) to aspirate a complementary volume of physiological saline solution from the bag 16; this saline solution volume allows the radioactive product to be diluted and also a sufficient injection volume to be obtained.

Next, the syringe 6 is drained by a suitable displacement of the syringe plunger 8 (downward). The radioactive product, possibly diluted with the complementary volume of physiological saline solution, then travels through the tube 24 where it is filtered by the devices 36, and then along the injection catheter 17 up to the patient.

Following this injection phase, the operator can possibly implement a complementary phase for rinsing the syringe body 7, the valve 15 and downstream pipes 17 and 24, with a volume of physiological saline solution suitable to ensure that the whole desired radioactive dose will be administered to the patient.

To that effect, the syringe plunger 8 is operated successively in aspiration (upward) to withdraw a definite volume of physiological saline solution from the bag 16, and then in ejection (downward) to eject this volume through the pipe 24 and the ejection catheter 17.

When the operator wants to replace the syringe 6 or the radioactive product source 11, he or she just has to operate the respective support structures 10 and 13. By way of information, the syringe 6 and the valve 15, with the different ways thereof, can be replaced following each injection. The syringe 6 on the one hand, and the valve 15 with its needle 20 and pipes 23, 24, the physiological saline solution bag 16 and the catheter 17 on the other hand, form a single-use sterile assembly that can be very easily replaced following each use.

The different afore-mentioned cycles of withdrawal, dilution and injection of this equipment are managed by computer and/or electronic control means, of the programmable controller type, able to drive automatically in a suitable manner the operating means 34 of the syringe plunger 8 and the three-way valve 15.

Whole of these cycles can be fully automated. According to the needs, or the wishes of the operator, injection of the radioactive dose to the patient can also be performed manually thanks to the disengageable means of the gear motor 34.

Figure 2:
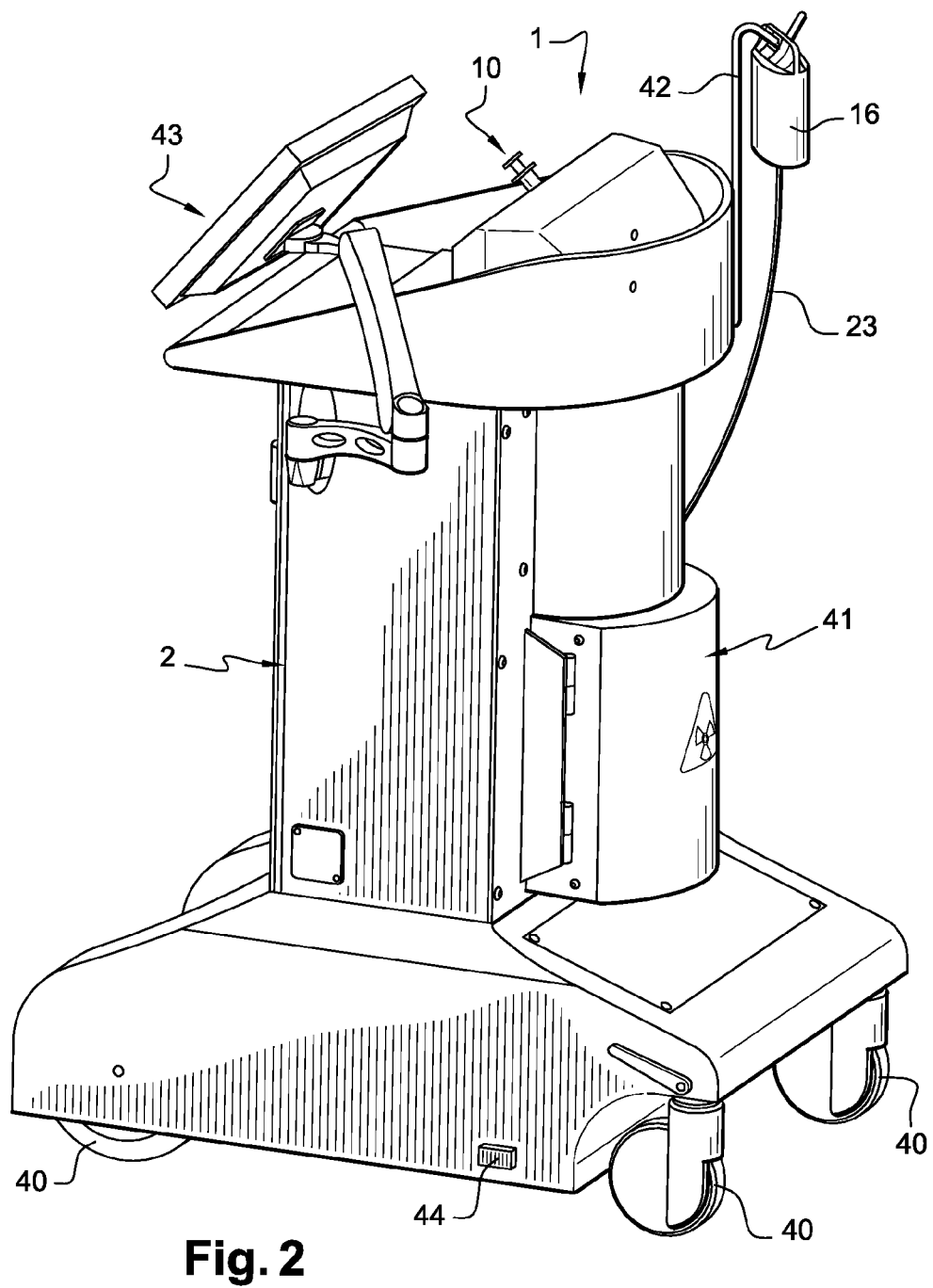
FIG. 2 is a perspective view of the external structure of a possible embodiment of the medical unit illustrated in FIG. 1.

A particularly interesting form of the medical unit schematically illustrated in FIG. 1 is shown in FIG. 2.

In FIG. 2, the shielded enclosure 2, which integrates the whole above-mentioned functional equipment, is mounted on a frame equipped with four wheels 40. Preferably, at least some of the wheels 40 are associated with a motor system providing a simple movement assist, or ensuring itself the autonomous moving of the mobile unit, remotely driven by a suitable joystick control unit.

The mobile unit 1 can also integrate a geolocation system, for example of the GPS type, so as to continuously know the remote location thereof inside a building.

It can be noticed the presence, in the lower part of the enclosure 2, of a shielded trap door 41 providing access to the inside of the sub-enclosure 2c, for installation or removal of the shielded container 12 enclosing the radioactive production source 11 on/from the support 13 thereof (in particular, when this support 13 is in low installing/removing position).

In the upper part, we can see the syringe support 10, the physiological saline solution bag 16 hanging from a support 42, as well as a touch-screen control and display board 43 that integrates the cycle management programmable controller or that is in direct relation with it (for example, being shifted in the unit frame). This control, dialogue and display board 43 allows the calibration operations (activity measurement) to be performed and the various phases of transfer preparation (dilution . . . ) and radioactive product injection to be viewed in real time.

The corresponding computer and/or electronic control means are equipped with connectics 44 for sending and/or receiving data, in particular for some exchanges with a computer server located at a nearby or a remote location (for example through an Intranet network or Internet), notably to perform a remote maintenance and to collect data concerning the patient (notably data necessary for determining the dose of radioelements that must be administered to him/her).

The frame of the unit 1 also carries its own power supply means, for example of the rechargeable battery type, ensuring the electric supplying, notably for the motor-driven wheels 40 and the computer and/or electronic control means.

This shielded mobile unit 1 forms a stand-alone unit enabling calibration and injection of any radioactive products (in particular, FDG). It is very compact-size because of the stacking of the activimeter, the three-way valve and the source of radioactive product on the same vertical axis or substantially on the same vertical axis, and because of the stacking of the sub-enclosures 2a, 2b and 2c. This unit allows fully secure withdrawal, measuring and injection operations.

The invention claimed is:

1. A medical unit for withdrawal, calibration, dilution and/or injection of a radioactive product that can be injected to a patient, the medical unit comprising:
   a container support configured to support a container made of a radioprotective material, the container support being configured to accommodate a source or a generator of injectable radioactive product;
   a syringe support configured to support a syringe equipped with a plunger;
   an activimeter configured to measure in real time radioisotopic activity from contents of said syringe;
   a system of pipes associated with at least one three-way valve for hydraulic connection of said radioactive product source, of said syringe, of a source of physiological saline solution and of an injection catheter configured to connect to the patient, the three-way valve comprising an upper way configured to connect to the syringe,
      a lower way configured to connect to the radioactive product source, and
      a side way provided with a Y-connector, the sideway configured to be connected to a first pipe connected to the saline solution source and to a second pipe connected to the injection catheter, a first check valve being provided in the first pipe and a second check valve being provided in the second pipe; and
   a shielded enclosure made of at least one radioprotective material in which the container support, the syringe support, the activimeter, the three-way valve and at least part of the system of pipes are disposed,
   wherein said three-way valve and said syringe plunger are configured to be operated to control aspiration of said radioactive product or said physiological saline solution into said syringe, and to control ejection, through said injection catheter, of said radioactive product, said physiological saline solution or a mixture of the radioactive product and the physiological saline solution, before the radioactive product, the physiological saline solution or the mixture are aspirated into said syringe, a dose of radioactive product withdrawn and injected by said syringe being measured by said activimeter,
   the syringe support, said three-way valve and said container support are arranged vertically relative to one another, respectively from top to bottom, said syringe support being configured to carry said syringe with the plunger thereof oriented upward,
   the three-way valve is fixedly secured inside the shielded enclosure on a substantially vertical axis running through the syringe and the radioactive product source, the upper way of the three-way valve facing the syringe, the lower way facing the radioactive product source, the side way oriented laterally, and
   the three-way valve being configured into two communication positions, the upper way and the lower way being in communication in a first communication position of the three-way valve to enable withdrawal of the dose of radioactive product into a body of the syringe, the upper way and the side way being in communication in a second communication position of the three-way valve to selectively enable one of aspiration of saline solution from the saline solution source into the syringe body during an aspiration operation by the syringe and ejection of material contained in the syringe body into the injection catheter during a draining operation of the syringe body.

2. The medical unit according to claim 1, wherein the activimeter has a generally tubular shape circumscribing a vertical-axis central well configured to contain the syringe, said activimeter being provided with an upper opening and a lower opening, the lower opening being orientated opposite the three-way valve and the container support.

3. The medical unit according to claim 2, wherein the upper way of the three-way valve, configured to connect to the syringe comprises a tight membrane seal configured to be pierced by a needle fit into said syringe.

4. The medical unit according to claim 2, wherein the lower way of the three-way valve, configured to connect to the radioactive product source is extended with a needle configured to pierce a membrane seal closing e a vial of the radioactive product source.

5. The medical unit according to claim 1, wherein the upper way of the three-way valve, configured to connect to the syringe, comprises a tight membrane seal configured to be pierced by a needle fit into said syringe.

6. The medical unit according to claim 5, wherein the lower way of the three-way valve, configured to connect to the radioactive product source is extended with a needle configured to pierce a membrane seal closing a vial of the radioactive product source.

7. The medical unit according to claim 1, wherein the first lower way of the three-way valve, configured to connect to the radioactive product source, is extended with a needle configured to pierce a membrane seal closing a vial of the radioactive product source.

8. The medical unit according to claim 1, wherein the container support and the syringe support are configured to move along the substantially vertical axis between a first position in which an operator can install or remove the radioactive product source and the syringe onto the respective container support and syringe support thereof, and a second position in which the radioactive product source and the syringe are connected to the three-way valve.

9. The medical unit according to claim 8, wherein the syringe support moves vertically through an orifice arranged in the shielded enclosure between the first position and the second position, the syringe support being located at least partially outside said shielded enclosure in the first position, and positioned inside a central well of the activimeter connected to the three-way valve in the second position.

10. The medical unit according to claim 9, wherein the container support moves inside the shielded enclosure between the first position and the second position, said shielded enclosure being provided with a front trap door configured to open to allow an operator to reach said container support at least when the container support is in the first position.

11. The medical unit according to claim 8, wherein the container support moves inside the shielded enclosure between the first position and the second position, said shielded enclosure being provided with a front trap door configured to open to allow an operator to reach said container support at least when the container support is in the first position.

12. The medical unit according to claim 1, further comprising:
one or more of a computer and an electronic controller configured to drive the three-way valve (15) and a means for operating the syringe plunger to perform the withdrawal and ejection operations of the syringe.

13. The medical unit according to claim 12, wherein the means for operating the syringe plunger comprises a disengageable gear motor configured to be controlled by the one or more of the computer and the electronic controller to enable automatic withdrawal of a definite dose of radioactive product into said syringe and to enable one of automatic and manual injection of the definite dose to the patient.

14. The medical unit according to claim 12, wherein the one or more of the computer and the electronic controller is provided with connectors for sending and/or receiving data in exchanges with a computer server.

15. The medical unit according to claim 1, wherein the shielded enclosure comprises three sub-enclosures aligned vertically relative to one another, an upper sub-enclosure housing the syringe and the activimeter, an intermediate sub-enclosure housing the valve, a lower sub-enclosure housing the radioactive product source, the sub-enclosures being connected together two by two via through-openings through which pass one or more of the pipes.

16. The medical unit according to claim 1, wherein the medical unit is mounted on wheels to be rendered mobile.

17. The medical unit according to claim 16, further comprising a geolocation system.

18. A single-use sterile assembly for a medical unit according to claim 1, wherein the upper way comprises a tight membrane seal configured to be pierced by a needle fit into said syringe, and
the lower way is extended with a needle configured to pierce a membrane seal closing a vial radioactive product source.

19. The single-use sterile assembly according to claim 18, wherein the first and second pipes are both configured to connect to the Y-connector.

* * * * *

UNITED STATES PATENT AND TRADEMARK OFFICE
CERTIFICATE OF CORRECTION

PATENT NO. : 8,439,815 B2 Page 1 of 1
APPLICATION NO. : 12/443272
DATED : May 14, 2013
INVENTOR(S) : Pierre-Marie Lemer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1024 days.

Signed and Sealed this
Eighth Day of September, 2015

Michelle K. Lee
*Director of the United States Patent and Trademark Office*